United States Patent
Zhang et al.

(10) Patent No.: US 10,669,274 B2
(45) Date of Patent: Jun. 2, 2020

(54) AZAPHENALENE-3-ONE DERIVATIVE, PREPARATION METHOD THEREFOR, AND APPLICATION THEROF

(71) Applicant: SUZHOU KANGRUN PHARMACEUTICALS INC., Wujiang (CN)

(72) Inventors: Hao Zhang, Wujiang (CN); Xiaodong Wang, Wujiang (CN); Weiliang Xu, Wujiang (CN); Weizheng Xu, Wujiang (CN)

(73) Assignee: SUZHOU KANGRUN PHARMACEUTICALS INC., Suzhou (CN)

( * ) Notice: Subject to any disclaimer, the term of this patent is extended or adjusted under 35 U.S.C. 154(b) by 0 days.

(21) Appl. No.: 16/497,773

(22) PCT Filed: May 24, 2018

(86) PCT No.: PCT/CN2018/088201
§ 371 (c)(1),
(2) Date: Sep. 25, 2019

(87) PCT Pub. No.: WO2018/177444
PCT Pub. Date: Oct. 4, 2018

(65) Prior Publication Data
US 2020/0031828 A1  Jan. 30, 2020

(30) Foreign Application Priority Data
Mar. 31, 2017 (CN) .......................... 2017 1 0205740

(51) Int. Cl.
*C07D 471/16* (2006.01)
(52) U.S. Cl.
CPC ................. *C07D 471/16* (2013.01)

(58) Field of Classification Search
CPC .................................................. C07D 471/16
See application file for complete search history.

(56) References Cited

FOREIGN PATENT DOCUMENTS

| CN | 102341394 A | 2/2012 |
| CN | 103703004 A | 4/2014 |
| CN | 106083849 A | 11/2016 |
| CN | 106883232 A | 6/2017 |

*Primary Examiner* — Paul V Ward
(74) *Attorney, Agent, or Firm* — SZDC Law P.C.

(57) ABSTRACT

Disclosed are an azaphenalene-3-one derivative, its preparation method and its application, in the field of pharmaceutical synthesis. The derivative has the following Formula (I), wherein R is H, 2-fluoroethylamino, 2,2,2-trifluoroethylamino, diethylamino, pyrrolidinyl, imidazolyl, piperidinyl, morphinolinyl, 4-methylaminopiperidinyl, 4-dimethylaminopiperidinyl, (1-methylpiperidin-4-yl)methylamino, (1-phenylpiperidin-4-yl)methylamino, (1-benzylpiperidin-4-yl)methylamino, or 7-fluoro-3,4-dihydroisoquinoline-2 (1H)-yl. The preparation method of the azaphenalene-3-one derivative is simple, the yield is high, post-treatment is easy, and purity is high. The derivative has high inhibitory activity against PARP enzyme. It establishes a foundation for researching better anti-tumor drugs using PARP inhibitors.

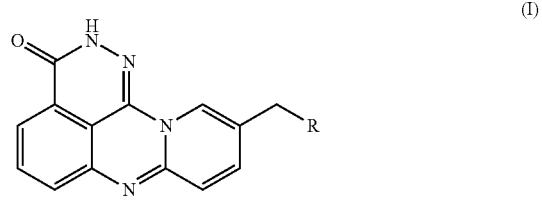

(I)

5 Claims, No Drawings

AZAPHENALENE-3-ONE DERIVATIVE, PREPARATION METHOD THEREFOR, AND APPLICATION THEROF

This application is the National Stage Application of PCT/CN2018/088201, filed on May 24, 2018, which claims priority to Chinese Patent Application No.: 201710205740.2, filed on Mar. 31, 2017, which is incorporated by reference for all purposes as if fully set forth herein.

FIELD OF THE INVENTION

The present invention relates to the field of pharmaceutical synthesis, and in particular, to an azaphenalene-3-one derivative and its preparation and application.

BACKGROUND OF THE INVENTION

Poly(adenosinediphosphate-ribose)-polymerase (poly (ADP-ribose)-polymerase, PARP) is a new target for cancer therapy, which catalyzes and transfers ADP-ribose units from nicotinamide adenine Dinucleotide (NAD+) to various receptor proteins. PARP is involved in DNA repair and transcriptional regulation. It not only plays a key role in regulating cell survival and death, but also is the main transcription factor in tumor development and inflammation.

PARP-1 is the first discovered member of the PARP family and has been extensively researched. It is a ribozyme consisting of 1014 amino acid residues, has a relative molecular mass of 116 ku, and plays a leading role in single-strand DNA repair. As a DNA gap receptor, PARP-1 is activated after DNA damage, recognizes and binds to DNA damage site, reduces DNA recombination, and prevents damaged DNA from being affected by exonuclease. After binding to the DNA damage site, the catalytic activity of PARP-1 is increased 10-fold to 500-fold, and NAD+ is catalytically decomposed into nicotinamide and ADP ribose by autoglycosylation and formation of a homodimer. Using ADP ribose as a substrate, the nuclear receptor protein (mainly PARP itself) forms a linear or linear PARP-1-ADP ribose polymer. These poly ADP ribose polymers with more negative charge and higher steric hindrance can not only prevent the nearby DNA molecules from recombining with the damaged DNA, but also reduce the affinity of PARP-1 to DNA, dissociating PARP-1 from the DNA damage site and guiding DNA repair enzyme to bind to the DNA damage site to repair the damage site. The dissociated PARP-1-ADP ribose polymer is cleaved by poly(ADP-ribose) glycohydrolase (PARG), and the lysed ADP ribose is re-used for synthesizing NAD+. After PARP-1 was dissociated from the ADP ribose polymer, it is reactivated and bound to DNA, and the DNA damage repair process is repeated. However, the over-expression of DNA repair enzymes in tumor cells activates its own DNA damage repair mechanism, which in turn produces resistance during drug therapy and radiation therapy. Studies have found that PARP inhibitors can block the DNA repair pathway and reduce the self-repairing ability of tumor cells. Therefore, the combination of PARP inhibitors and chemoradiotherapy can effectively enhance the anti-tumor effect. The studies also found that PARP inhibitors alone have a significant inhibitory effect on breast cancer and ovarian cancer with BRCA1/2 gene deletion or mutation.

In summary, PARP inhibitor has broad application in antitumor research and therapy. Chinese Patent Application No. 2015102677321 discloses azaphenalene-3-one derivative, a process for preparing the same and its application as a PARP inhibitor. The azaphenalene-3-one derivative has the following structure:

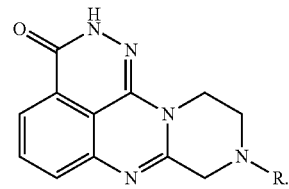

In the structure, R is hydrogen, methyl, ethyl, isopropyl, benzyl or 3-methyl-3-butenyl. The azaphenalene-3-one derivative has a high activity of inhibiting PARP enzyme, and can be used as a good foundation for the development of azaphenalene-3-one derivative as PARP inhibitors to treat tumor, but its synthesis is difficult. The yield and product purity are low, and post-treatment is difficult. In the synthetic route, toxic reagents, such as acetic anhydride, phosphorus oxychloride and sulfuric acid, were used. The number of compounds prepared was small, and the success rate was low, which is not suitable for screening of a large number of compounds. Therefore, based on the previous research, the present invention intends to design and synthesize a series of new azaphenalene-3-one derivatives based on pyridazinone nucleus. Preliminary study of their activity was also conducted, which establishes a good foundation for researching better anti-tumor drugs.

SUMMARY OF THE INVENTION

Technical Problem to be Solved: The present invention provides an azaphenalene-3-one derivative, its preparation method and application thereof. The preparation method is simple and provides high yield, easy post-treatment, and high purity product. The azaphenalene-3-one derivatives prepared has high activity of inhibiting PARP enzyme and provide a basis for developing more active anti-tumor drugs.

Technology Solution: An azaphenalene-3-one derivative has the following Formula (I):

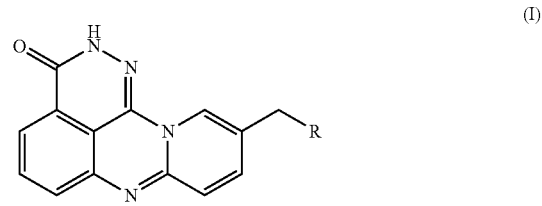

R is H, 2-fluoroethylamino, 2,2,2-trifluoroethylamino, diethylamino, pyrrolidinyl, imidazolyl, piperidinyl, morphinolinyl, 4-methylaminopiperidinyl, 4-dimethylaminopiperidinyl, (1-methylpiperidin-4-yl)methylamino, (1-phenylpiperidin-4-yl)methylamino, (1-benzylpiperidin-4-yl) methylamino, or 7-fluoro-3,4-dihydroisoquinoline-2(1H)-yl.

A method of preparing the azaphenalene-3-one derivative includes the following steps:

(1) adding pyridine to a mixture of 2-amino-6-methoxybenzoic acid and acetonitrile, and adding triphosgene to the mixture while maintaining a reaction temperature not exceeding 30° C., a molar ratio of 2-amino-6-methoxybenzoic acid:pyridine:triphosgene being 1:2:0.3, a ratio of acetonitrile:reactants being 10 mL:1 g, reacting at room temperature for 5.5-8 hours, filtering the mixture and drying to obtain compound 2:

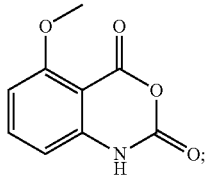

(2) adding sodium hydroxide in two batches to a mixture of compound 2 and methanol, a molar ratio of compound 2: sodium hydroxide being 1:0.1, a ratio of methanol:reactants being 10 mL:1 g, reacting at 50-70° C. for 1.5-3 hours, removing methanol after reaction is complete, extracting with ethyl acetate and water, colleting ethyl acetate, removing ethyl acetate, purifying with column chromatograph to obtain compound 3:

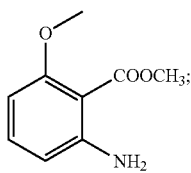

(3) adding 2-bromo-5-methylpyridine, cesium carbonate, palladium acetate, and 4,5-bisdiphenylphosphino-9,9-dimethyloxaxene to a mixture of compound 3 and dioxane, a molar ratio of compound 3:2-bromo-5-methylpyridine:cesium carbonate:palladium acetate:4,5-bisdiphenylphosphino-9,9-dimethyloxaxene being 1:1.1:1.5:0.1:0.3, a ratio of dioxane:reactants being 10 mL:1 g, reacting under nitrogen atmosphere at 50-75° C. for 5.5-8 hours, extracting with water and methylene chloride after reaction is complete, collecting methylene chloride, removing methylene chloride, purifying with column chromatograph to obtain compound 4:

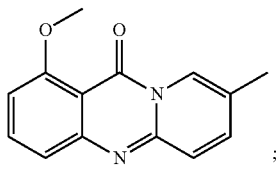 [SMILES: COc1cccc2nc3ccc(C)cn3c(=O)c12]

(4) adding compound 4 to methylene chloride to form a mixture, diluting boron tribromide with methylene chloride, adding diluted boron tribromide to the mixture while maintaining a reaction temperature not exceeding −20° C., a molar ratio of compound 4:boron tribromide being 1:2.2, a ratio of methylene chloride:reactants being 20 mL:1 g, methylene chloride being divided into 2 parts: first part being mixed with compound 4 and second part being diluted with boron tribromide, reacting at −5--15° C. for 2.5-4 hours, quenching reaction with water while maintaining a reaction temperature not exceeding −10° C., raising the reaction temperature to room temperature, adjusting pH to neutral with saturated sodium carbonate solution, extracting with water and methylene chloride, collecting methylene chloride, drying, removing methylene chloride to obtain compound 5:

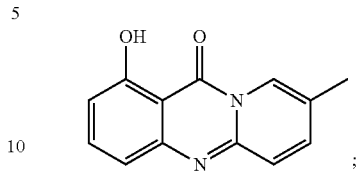

(5) adding 4-dimethylaminopyridine to a mixture of compound 5 and methylene chloride, diluting trifluoromethanesulfonic anhydride with methylene chloride, adding diluted trifluoromethanesulfonic anhydride to the mixture while maintaining a reaction temperature not exceeding −5° C., a molar ratio of compound 5: trifluoromethanesulfonic anhydride:4-dimethylaminopyridine being 1:1.2:1.6, a ratio of methylene chloride:reactants being 20 mL:1 g, methylene chloride being divided into two parts: first part being mixed with compound 5 and second part being diluted with trifluoromethanesulfonic anhydride, reacting at room temperature, adjusting pH to weakly acidic with HCl, extracting with water and methylene chloride, collecting methyl chloride, drying, removing methylene chloride, purifying with column chromatography to obtain compound 6:

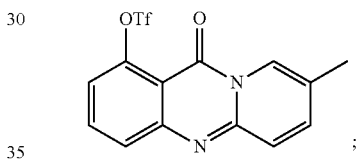

(6) adding [1,1'-bis(diphenylphosphino)ferrocene]palladium dichloride and triethylamine to a mixture of compound 6, methanol, and N,N-dimethylformamide, [1,1'-bis(diphenylphosphino)ferrocene]palladium dichloride being a weight of 10% of the weight of compound 6, a molar ratio of compound 6: triethylamine being 1:3, a ratio of methanol and N,N-dimethylformamide:reactants being 10 mL:1 g, a volume ratio of methanol:N,N-dimethylformamide being 4:1, reacting with CO at 65-85° C. and under 0.8 MPa for 7.5-10 hours, removing methanol and N,N-dimethylformamide after reaction is complete, extracting with water and methylene chloride, collecting methylene chloride, drying, removing methylene chloride, purifying with column chromatograph to obtain compound 7:

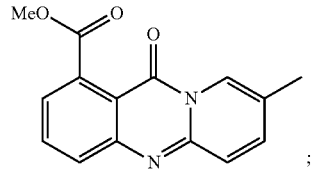 [SMILES: COC(=O)c1cccc2nc3ccc(C)cn3c(=O)c12]

(7) when R is H, adding hydrazine hydrate to a mixture of compound 7 and ethanol, a molar ratio of compound 7: hydrazine hydrate being 1:2, a ratio of ethanol:reactant being 10 mL:1 g, reacting at room temperature for 5.5-8 hours, removing ethanol and hydrazine hydrate after reaction is complete, adding water and stirring, filtering to obtain compound 8:

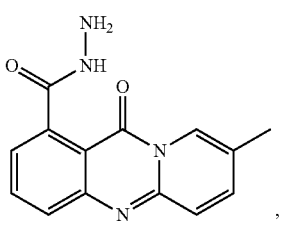 [SMILES: Cc1ccc2nc3cccc(C(=O)NN)c3c(=O)n2c1]

adding polyphosphoric acid to compound 8, a ratio of polyphosphoric acid:compound 8 being 10 mL:1 g, reacting at 130-150° C. for 5.5-8 hours, quenching with water, adjusting pH to weakly basic with ammonia to form participation, filtering to obtain compound 9:

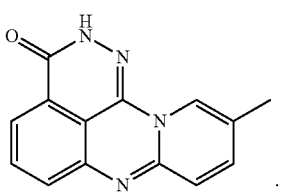 [SMILES: CC1=CN2C(=Nc3cccc4c(=O)[nH]nc2c34)C=C1]

A method of preparing the azaphenalene-3-one derivative includes the following steps:

(1) adding pyridine to a mixture of 2-amino-6-methoxybenzoic acid and acetonitrile, and adding triphosgene to the mixture while maintaining a reaction temperature not exceeding 30° C., a molar ratio of 2-amino-6-methoxybenzoic acid:pyridine:triphosgene being 1:2:0.3, a ratio of acetonitrile:reactants being 10 mL:1 g, reacting at room temperature for 5.5-8 hours, filtering the mixture and drying to obtain compound 2:

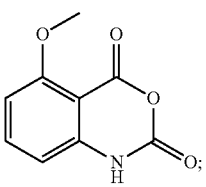

(2) adding sodium hydroxide in two batches to a mixture of compound 2 and methanol, a molar ratio of compound 2: sodium hydroxide being 1:0.1, a ratio of methanol:reactants being 10 mL:1 g, reacting at 50-70° C. for 1.5-3 hours, removing methanol after reaction is complete, extracting with ethyl acetate and water, colleting ethyl acetate, removing ethyl acetate, purifying with column chromatograph to obtain compound 3:

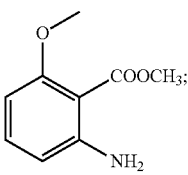

(3) adding 2-bromo-5-methylpyridine, cesium carbonate, palladium acetate, and 4,5-bisdiphenylphosphino-9,9-dimethyloxaxene to a mixture of compound 3 and dioxane, a molar ratio of compound 3:2-bromo-5-methylpyridine:cesium carbonate:palladium acetate:4,5-bisdiphenylphosphino-9,9-dimethyloxaxene being 1:1.1:1.5:0.1:0.3, a ratio of dioxane:reactants being 10 mL:1 g, reacting under nitrogen atmosphere at 50-75° C. for 5.5-8 hours, extracting with water and methylene chloride after reaction is complete, collecting methylene chloride, removing methylene chloride, purifying with column chromatograph to obtain compound 4:

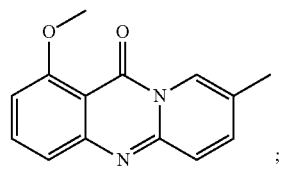 [SMILES: COc1cccc2nc3ccc(C)cn3c(=O)c12]

(4) adding compound 4 to methylene chloride to form a mixture, diluting boron tribromide with methylene chloride, adding diluted boron tribromide to the mixture while maintaining a reaction temperature not exceeding −20° C., a molar ratio of compound 4: boron tribromide being 1:2.2, a ratio of methylene chloride:reactants being 20 mL:1 g, methylene chloride being divided into 2 parts: first part being mixed with compound 4 and second part being diluted with boron tribromide, reacting at −5−−15° C. for 2.5-4 hours, quenching reaction with water while maintaining a reaction temperature not exceeding −10° C., raising the reaction temperature to room temperature, adjusting pH to neutral with saturated sodium carbonate solution, extracting with water and methylene chloride, collecting methylene chloride, drying, removing methylene chloride to obtain compound 5:

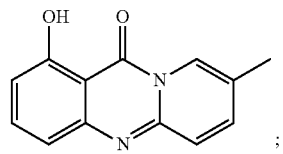 [SMILES: Cc1ccc2nc3cccc(O)c3c(=O)n2c1]

(5) adding 4-dimethylaminopyridine to a mixture of compound 5 and methylene chloride, diluting trifluoromethanesulfonic anhydride with methylene chloride, adding diluted trifluoromethanesulfonic anhydride to the mixture while maintaining a reaction temperature not exceeding −5° C., a molar ratio of compound 5: trifluoromethanesulfonic anhydride:4-dimethylaminopyridine being 1:1.2:1.6, a ratio of methylene chloride:reactants being 20 mL:1 g, methylene chloride being divided into two parts: first part being mixed with compound 5 and second part being diluted with trifluoromethanesulfonic anhydride, reacting at room temperature, adjusting pH to weakly acidic with HCl, extracting with water and methylene chloride, collecting methyl chloride, drying, removing methylene chloride, purifying with column chromatography to obtain compound 6:

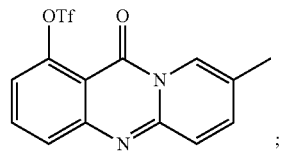 [SMILES: Cc1ccc2nc3cccc(OS(=O)(=O)C(F)(F)F)c3c(=O)n2c1]

(6) adding [1,1'-bis(diphenylphosphino)ferrocene]palladium dichloride and triethylamine to a mixture of compound 6, methanol, and N,N-dimethylformamide, [1,1'-bis(diphenylphosphino)ferrocene]palladium dichloride being a weight of 10% of the weight of compound 6, a molar ratio of compound 6: triethylamine being 1:3, a ratio of methanol and N,N-dimethylformamide:reactants being 10 mL:1 g, a volume ratio of methanol:N,N-dimethylformamide being 4:1, reacting with CO at 65-85° C. and under 0.8 MPa for 7.5-10 hours, removing methanol and N,N-dimethylformamide after reaction is complete, extracting with water and methylene chloride, collecting methylene chloride, drying, removing methylene chloride, purifying with column chromatograph to obtain compound 7:

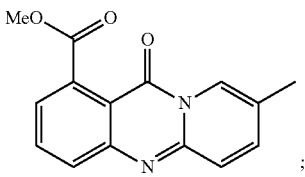 [SMILES: COC(=O)c1cccc2nc3ccc(C)cn3c(=O)c12]
;

(7) when R is not H, when R is not H, adding N-bromosuccinimide and azobisisobutyronitrile to a mixture of compound 7 and carbon tetrachloride, refluxing the mixture for 9.5-12 hours, the molar ratio of compound 7: N-bromosuccinimide:azobisisobutyronitrile being 1:1.2:0.1, a ratio of carbon tetrachloride:reactants being 20 mL:1 g, extracting with water and methylene chloride, collecting methylene chloride, drying, removing methylene chloride, purifying with column chromatograph to obtain compound 10:

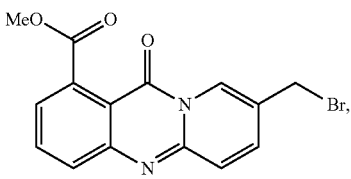

adding a coupling compound and potassium carbonate to a mixture of compound 10 and acetonitrile, a molar ratio of compound 10: the coupling compound:potassium carbonate being 1:1.1:4, a ratio of acetonitrile:reactants being 10 mL:1 g, reacting at 35-55° C. for 5.5-8 hours, extracting with water and ethyl acetate, collecting ethyl acetate, drying, and removing ethyl acetate to obtain compound 11:

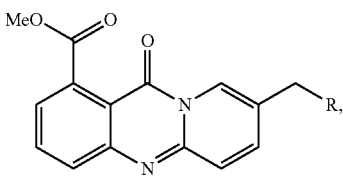

wherein the coupling compound is 2-fluoroethylamine hydrochloride, 2,2,2-trifluoroethylamine hydrochloride, diethylamine hydrochloride, pyrrolidine, imidazole, piperidine, morpholine, 4-tert-butoxycarbonylaminopiperidine, 4-dimethylaminopiperidine, 1-methyl-4-methylaminopiperidine, 1-phenyl-4-methylaminopiperidine, 1-benzyl-4-methylaminopiperidine or 7-fluoro-1,2,3,4-tetrahydroisoquinoline, adding hydrazine hydrate to a mixture of compound 11 and ethanol, a molar ratio of hydrazine hydrate:compound 11 being 2:1, a ratio of ethanol:reactant being 10 mL:1 g, reacting at room temperature for 5.5-8 hours, removing ethanol and hydrazine hydrate after reaction is complete, adding water and stirring, filtering to obtain compound 12:

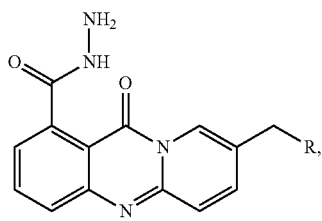

adding polyphosphoric acid to compound 12, a ratio of polyphosphoric acid:compound 8 being 10 mL:1 g, reacting at 130-150° C. for 5.5-8 hours, quenching with water, adjusting pH to weakly basic with ammonia to form participation, filtering to obtain compound 13:

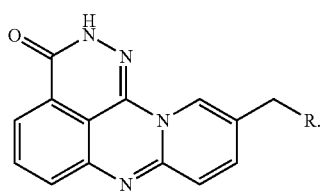

Preferably, the completion of the reaction is monitored by thin layer chromatography.

Use of the azaphenalene-3-one derivative as a PARP inhibitor.

Advantages

1. By screening and preliminary researching the activity of the azaphenalene-3-one derivative prepared with various coupling compounds, the inhibitory activity against PARP enzyme reaches nM level (at the same level as the leading compounds in clinical trials). This provides a good direction for the subsequent research.

2. Compared with the prior art, the structure of the azaphenalene-3-one derivative of the present application has a conjugated pyridine ring. The derivatives are more stable, and the raw materials used are less expensive. The synthetic route is mild and environmentally friendly.

3. The derivatives have excellent inhibitory effect on PARP enzyme and can be used as PARP inhibitors.

DETAILED DESCRIPTION OF THE ILLUSTRATED EMBODIMENTS

The invention will now be further described in conjunction with specific embodiments.

The synthesis process of the azaphenalene-3-one derivative described in the present application is as follows:

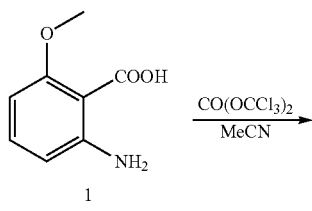

-continued
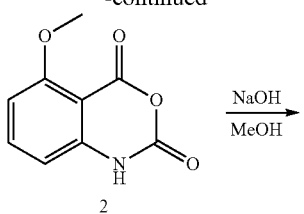
2
NaOH / MeOH →
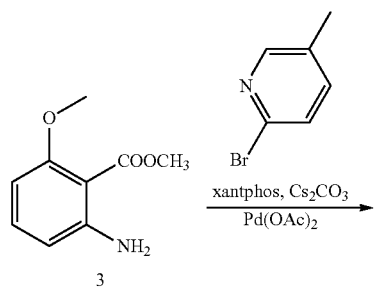
3
+ 
5-methyl-2-bromopyridine
xantphos, Cs₂CO₃ / Pd(OAc)₂ →
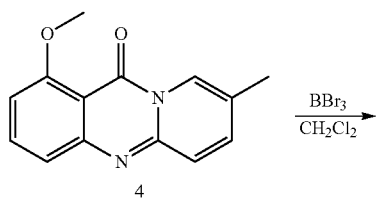
4
BBr₃ / CH₂Cl₂ →
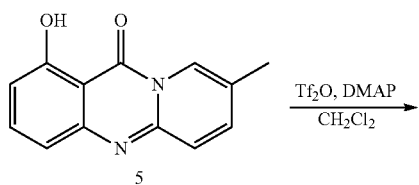
5
Tf₂O, DMAP / CH₂Cl₂ →
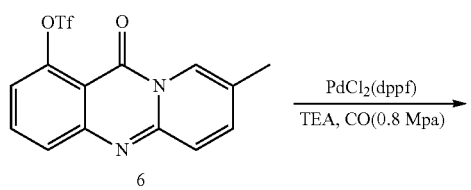
6
PdCl₂(dppf) / TEA, CO(0.8 Mpa) →
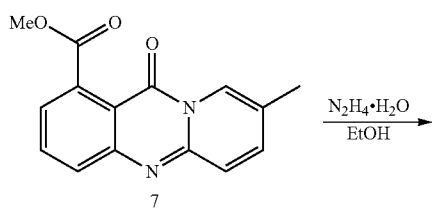
7
N₂H₄·H₂O / EtOH →
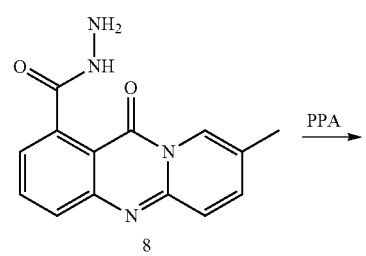
8
PPA →
-continued
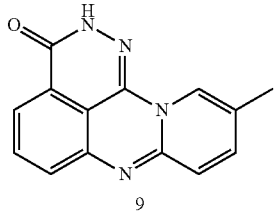
9
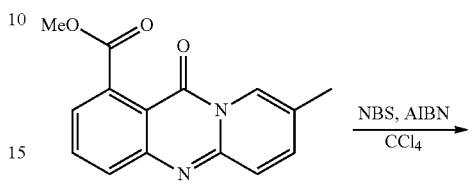
7
NBS, AIBN / CCl₄ →
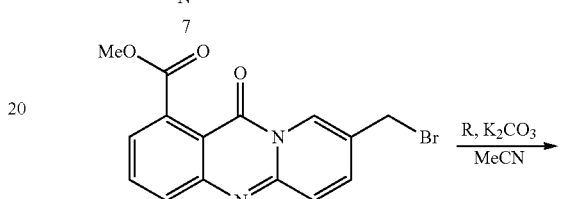
10
R, K₂CO₃ / MeCN →
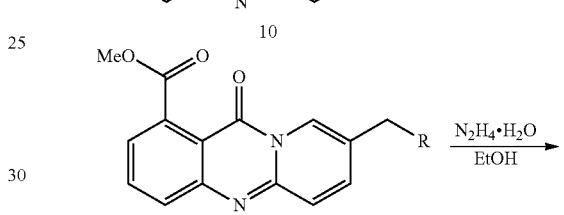
11
N₂H₄·H₂O / EtOH →
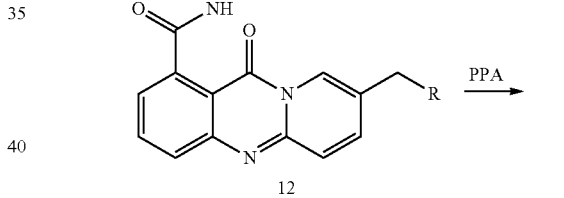
12
PPA →
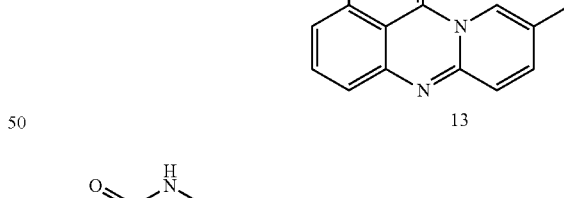
13
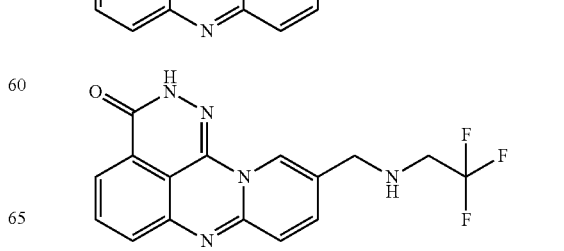
14
15

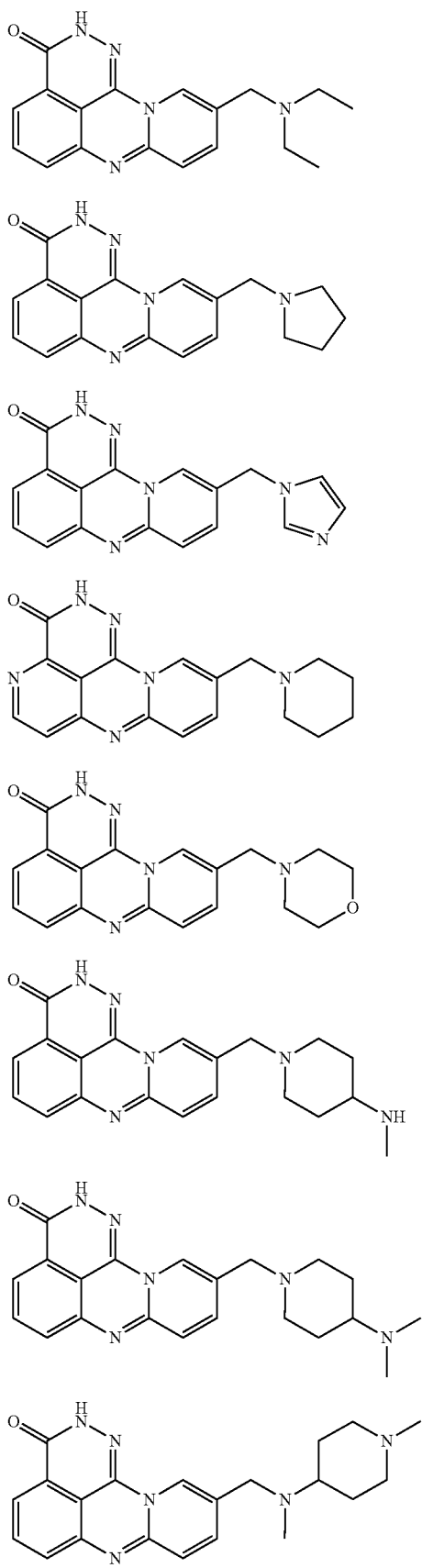

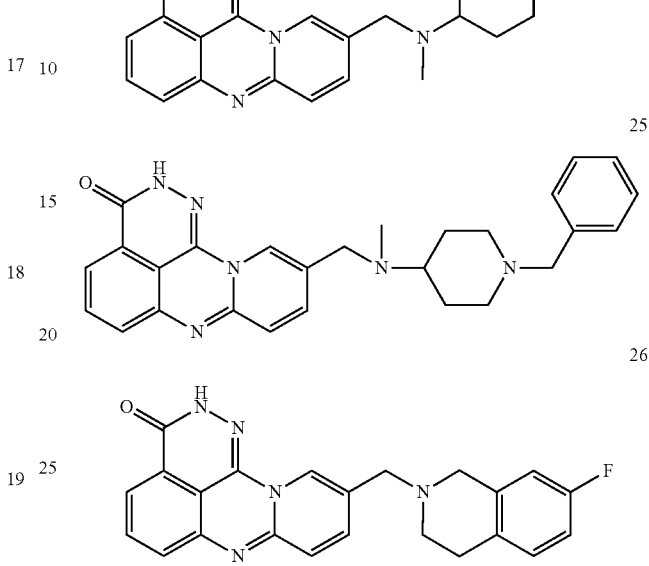

EXAMPLE 1

An azaphenalene-3-one derivative has the following Formula (I):

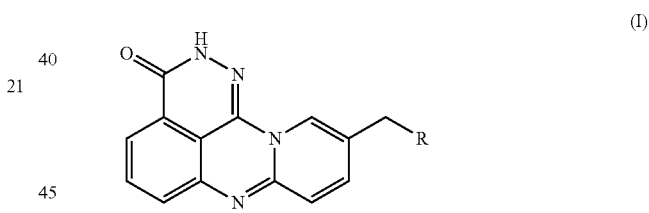

(I)

R is H, 2-fluoroethylamino, 2,2,2-trifluoroethylamino, diethylamino, pyrrolidinyl, imidazolyl, piperidinyl, morpholinyl, 4-methylaminopiperidinyl, 4-dimethylaminopiperidinyl, (1-methylpiperidin-4-yl)methylamino, (1-phenylpiperidin-4-yl)methylamino, (1-benzylpiperidin-4-yl)methylamino, or 7-fluoro-3,4-dihydroisoquinoline-2(1H)-yl.

The azaphenalene-3-one derivative can be prepared by the following steps:

(1) Preparation of Compound 2

Pyridine (67.86 g, 857.84 mmol) was added to a mixture of 2-amino-6-methoxybenzoic acid (71.7 g, 428.92 mmol) and acetonitrile (720 mL). Triphosgene (43.27 g, 145.83 mmol) was added to the mixture while maintaining a reaction temperature not exceeding 30° C. The mixture was reacted at room temperature for 5.5 hours. After thin layer chromatograph (TLC) indicated that reaction was complete, 1 L water was added, and the mixture was filtered and dried to obtain a yellow-white solid compound 2:

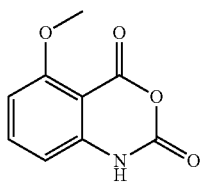

(70 g, 84%);

(2) Preparation of Compound 3

Sodium hydroxide (1.45 g, 36.24 mmol) was added in two batches to a mixture of compound 2 (70 g, 362.40 mmol) and methanol (700 mL). The mixture was reacted at 50° C. for 1.5 hours. After reaction was complete, methanol was removed. 500 ml Water and 1 L ethyl acetate were added and extracted twice. Ethyl acetate layer was collected, combined, dried, and concentrated. The remaining mixture was purified by column chromatograph to obtain compound 3 as a maroon solid:

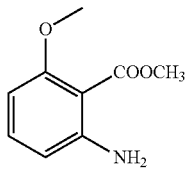

(52.1 g, 79%);

(3) Preparation of Compound 4

2-Bromo-5-methylpyridine (26.11 g, 151.77 mmol), cesium carbonate (66.08 g, 202.81 mmol), palladium acetate (0.90 g, 4.00 mmol), and 4,5-bisdiphenylphosphino-9,9-dimethyloxaxene (2.68 g, 4.63 mmol) were added to a mixture of compound 3 (25 g, 137.98 mmol) and dioxane (250 mL). The mixture was reacted under nitrogen atmosphere at 50° C. for 5.5 hours. After Thin Layer Chromatograph (TLC) indicated that the reaction was complete, 500 mL and 800 mL methylene chloride were added and extracted twice. Methylene chloride layer was collected, combined, dried and concentrated. The remaining mixture was purified by column chromatograph to obtain compound 4 as a light yellow solid:

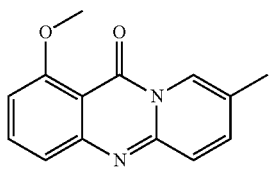 [SMILES: COc1cccc2nc3ccc(C)cn3c(=O)c12]

(24.6 g, 74%);

(4) Preparation of Compound 5

Compound 4 (24.6 g, 102.39 mmol) was added to methylene chloride (500 mL) to form a mixture. Boron tribromide (56.43 g, 225.25 mmol) was diluted with 110 mL methylene chloride. The diluted boron tribromide was added slowly to the compound 4 mixture while maintaining a reaction temperature not exceeding −20° C. Afterwards, the mixture was reacted at −5° C. for 2.5 hours. After TLC indicated that the reaction was complete, 150 mL water was added slowly to quench boron tribromide while maintaining a reaction temperature not exceeding −10° C. The reaction temperature was then raised to room temperature, and saturated sodium carbonate solution was added to the mixture to pH 7. 500 mL water and 800 mL methylene chloride were added and extracted once. Methylene chloride layer was collected, combined, dried and concentrated to obtain compound 5 as a yellow solid:

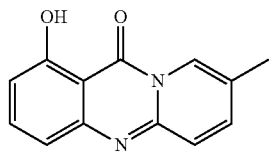 [SMILES: Cc1ccc2nc3cccc(O)c3c(=O)n2c1]

(20 g, 86%);

(5) Preparation of Compound 6

4-Dimethylaminopyridine (42.34 g. 346.55 mmol) was added to a mixture of compound 5 (49 g, 216.59 mmol) and methylene chloride (1 L). Trifluoromethanesulfonic anhydride (73.33 g, 259.91 mmol) was diluted with 150 mL methylene chloride. The diluted trifluoromethanesulfonic anhydride was added slowly to the mixture while maintaining a reaction temperature not exceeding −5° C. Afterwards, the reaction temperature was raised to room temperature, and the mixture was reacted for 0.5 hour. After TLC indicated that the reaction was complete, water (500 mL) and methylene chloride (500 mL) were added, and 1 mol/L HCl was added to adjust pH to 6. The mixture was then extracted twice. Methylene chloride layer was collected, combined, dried, and concentrated. The remaining mixture was purified by column chromatography to obtain compound 6 as a brownish yellow solid:

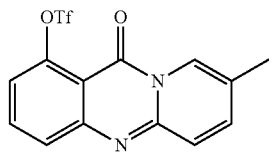 [SMILES: Cc1ccc2nc3cccc(OS(=O)(=O)C(F)(F)F)c3c(=O)n2c1]

(68.9 g, 69%);

(6) Preparation of Compound 7

[1,1'-Bis(diphenylphosphino)ferrocene]palladium dichloride (7 g, 9.57 mmol) and triethylamine (58.38 g, 576.90 mmol) were added to a mixture of compound 6 (68.9 g, 192.30 mmol), methanol/N,N-dimethylformamide (volume ratio of 4:1, 700 mL). The mixture was reacted under CO atmosphere (recharged 3 times) at 65° C. and under 0.8 MPa for 7.5 hours. After TLC indicated that the reaction was complete, solvent was removed. Water (500 mL) and methylene chloride (800 mL) were added and extracted twice. The methylene chloride layer was collected, combined, dried, and concentrated. The remaining mixture was purified by column chromatography to obtain compound 7 as a brownish yellow solid:

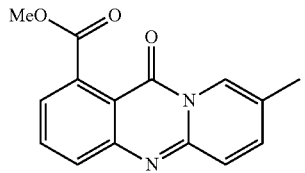 [SMILES: COC(=O)c1cccc2nc3ccc(C)cn3c(=O)c12]

(45.6 g, 88%);

(7) Preparation of Compound 8

Hydrazine hydrate (186.61 mg, 3.73 mg) was added to a mixture of compound 7 (500 mg, 1.86 mmol) and ethanol (5 mL). The mixture was reacted at room temperature for 5.5 hours. After TLC indicated that the reaction was complete, ethanol and hydrazine were removed. Water (20 mL) was added the mixture and the mixture was stirred. The mixture was filtered to obtain compound 8 as a yellow solid:

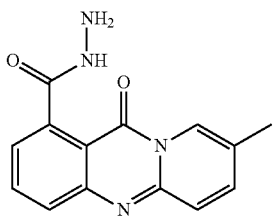 [SMILES: Cc1ccc2nc3cccc(C(=O)NN)c3c(=O)n2c1]

(408 mg, 82%);

(8) Preparation of Compound 9

Compound 8 from step (8) was added to 5 mL polyphosphoric acid, and the mixture was reacted at 130° C. for 5.5 hours. The mixture was poured into water (30 mL) to quench the polyphosphoric acid. Ammonia was added to the mixture to pH 8 while maintaining the temperature of the mixture not exceeding 30° C. Mixture was then filtered and dried to obtain compound 9 as a light yellow solid:

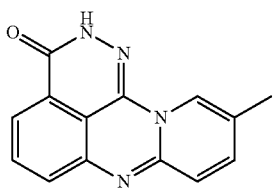 [SMILES: CC1=CN2C(=Nc3cccc4c(=O)[nH]nc2c34)C=C1]

(280 mg, 74%).

(9) Preparation of Compound 10

N-bromosuccinimide (19.79 g, 111.83 mmol) and azobisisobutyronitrile (1.53 g, 9.32 mmol) were added to a mixture of compound 7 (25 g, 93.19 mmol) and carbon tetrachloride (250 mL). The mixture was refluxed for 9.5 hours. After TLC indicates that the reaction was complete, water (500 mL) and methylene chloride (500 mL) were added and extracted twice. The methylene chloride layer was collected, combined, dried, and concentrated. The remaining mixture was purified by column chromatograph to obtain compound 10 as a golden compound:

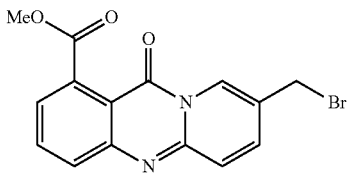 [SMILES: COC(=O)c1cccc2nc3ccc(CBr)cn3c(=O)c12]

(20 g, 62%);

(10) Preparation of Compounds 14-26 (Compound 14 used as example)

2-Fluoroethylamine hydrochloride (157.69 mg, 5.76 mmol) and potassium carbonate (796.18 mg, 5.76 mmol) were added to a mixture of compound 10 (500 mg, 1.44 mmol) and acetonitrile (5 mL). The mixture was reacted at 35° C. for 5.5 hours. After TLC indicated that the reaction was complete, water (50 mL) and ethyl acetate (100 mL) were added and extracted twice. The ethyl acetate layer was collected, combined, dried, and concentrated to obtain compound 11 as a yellow oil:

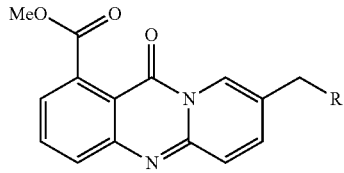

(380 mg, 80%);

Hydrazine hydrate (115.14 mg, 2.30 mmol) was added to a mixture of compound 11 from the above step and ethanol (5 mL). The mixture was reacted at room temperature for 5.5 hours. After TLC indicated that the reaction was complete, ethanol and hydrazine were removed. Water (50 mL) was added the mixture and the mixture was stirred. The mixture was filtered to obtain compound 12 as a yellow solid:

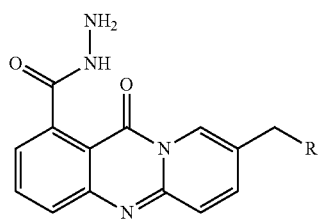

(287 mg, 76%).

Compound 12 from the above step was added to polyphosphoric acid (5 mL), and the mixture was reacted at 130° C. for 5.5 hours. The mixture was poured into water (30 mL) to quench the polyphosphoric acid. Ammonia was added to the mixture to pH 8 while maintaining the temperature of the mixture not exceeding 30° C. Mixture was then filtered and dried to obtain compound 14 as a light yellow solid (200 mg, 74%).

Replacing 2-fluoroethylamine hydrochloride with 2,2,2-trifluoroethylamine hydrochloride, diethylamine hydrochloride, pyrrolidine, imidazole, piperidine, morpholine, 4-tert-butoxycarbonylaminopiperidine, 4-dimethylaminopiperidine, 1-methyl-4-methylaminopiperidine, 1-phenyl-4-methylaminopiperidine, 1-benzyl-4-methylaminopiperidine or 7-fluoro-1,2,3,4-tetrahydroisoquinoline, other conditions remained the same, and compounds 15-26 were prepared. Note that, if the coupling compound is not a hydrochloride salt, the amount of potassium carbonate will be reduced by one equivalent.

EXAMPLE 2

An azaphenalene-3-one derivative has the following Formula (I):

(I)

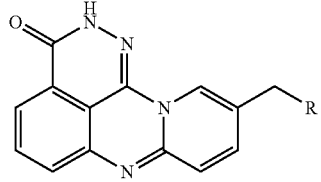

R is H, 2-fluoroethylamino, 2,2,2-trifluoroethylamino, diethylamino, pyrrolidinyl, imidazolyl, piperidinyl, morphinolinyl, 4-methylaminopiperidinyl, 4-dimethylaminopiperidinyl, (1-methylpiperidin-4-yl)methylamino, (1-phenylpiperidin-4-yl)methylamino, (1-benzylpiperidin-4-yl) methylamino, or 7-fluoro-3,4-dihydroisoquinoline-2(1H)-yl.

The azaphenalene-3-one derivative can be prepared by the following steps:

(1) Preparation of Compound 2

Pyridine (67.86 g, 857.84 mmol) was added to a mixture of 2-amino-6-methoxybenzoic acid (71.7 g, 428.92 mmol) and acetonitrile (720 mL). Triphosgene (43.27 g, 145.83 mmol) was added to the mixture while maintaining a reaction temperature not exceeding 30° C. The mixture was reacted at room temperature for 8 hours. After thin layer chromatograph (TLC) indicated that reaction was complete, 1 L water was added, and the mixture was filtered and dried to obtain a yellow-white solid compound 2:

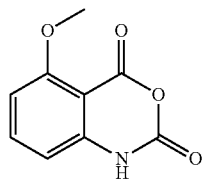

(70 g, 84%);

(2) Preparation of Compound 3

Sodium hydroxide (1.45 g, 36.24 mmol) was added in two batches to a mixture of compound 2 (70 g, 362.40 mmol) and methanol (700 mL). The mixture was reacted at 70° C. for 3 hours. After reaction was complete, methanol was removed. 500 ml Water and 1 L ethyl acetate were added and extracted twice. Ethyl acetate layer was collected, combined, dried, and concentrated. The remaining mixture was purified by column chromatograph to obtain compound 3 as a maroon solid:

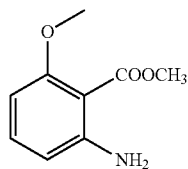

(52.1 g, 79%);

(3) Preparation of Compound 4

2-Bromo-5-methylpyridine (26.11 g, 151.77 mmol), cesium carbonate (66.08 g, 202.81 mmol), palladium acetate (0.90 g, 4.00 mmol), and 4,5-bisdiphenylphosphino-9,9-dimethyloxaxene (2.68 g, 4.63 mmol) were added to a mixture of compound 3 (25 g, 137.98 mmol) and dioxane (250 mL). The mixture was reacted under nitrogen atmosphere at 75° C. for 8 hours. After Thin Layer Chromatograph (TLC) indicated that the reaction was complete, 500 mL and 800 mL methylene chloride were added and extracted twice. Methylene chloride layer was collected, combined, dried and concentrated. The remaining mixture was purified by column chromatograph to obtain compound 4 as a light yellow solid:

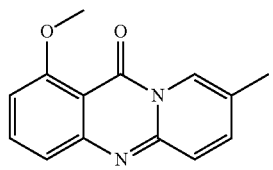 [SMILES: COc1cccc2nc3ccc(C)cn3c(=O)c12]

(24.6 g, 74%);

(4) Preparation of Compound 5

Compound 4 (24.6 g, 102.39 mmol) was added to methylene chloride (500 mL) to form a mixture. Boron tribromide (56.43 g, 225.25 mmol) was diluted with 110 mL methylene chloride. The diluted boron tribromide was added slowly to the compound 4 mixture while maintaining a reaction temperature not exceeding −20° C. Afterwards, the mixture was reacted at −15° C. for 4 hours. After TLC indicated that the reaction was complete, 150 mL water was added slowly to quench boron tribromide while maintaining a reaction temperature not exceeding −10° C. The reaction temperature was then raised to room temperature, and saturated sodium carbonate solution was added to the mixture to pH 7. 500 mL water and 800 mL methylene chloride were added and extracted once. Methylene chloride layer was collected, combined, dried and concentrated to obtain compound 5 as a yellow solid:

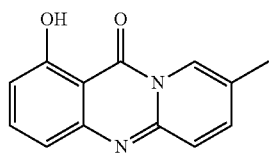 [SMILES: Cc1ccc2nc3cccc(O)c3c(=O)n2c1]

(20 g, 86%);

(5) Preparation of Compound 6

4-Dimethylaminopyridine (42.34 g. 346.55 mmol) was added to a mixture of compound 5 (49 g, 216.59 mmol) and methylene chloride (1 L). Trifluoromethanesulfonic anhydride (73.33 g, 259.91 mmol) was diluted with 150 mL methylene chloride. The diluted trifluoromethanesulfonic anhydride was added slowly to the mixture while maintaining a reaction temperature not exceeding −5° C. Afterwards, the reaction temperature was raised to room temperature, and the mixture was reacted for 0.5 hour. After TLC indicated that the reaction was complete, water (500 mL) and methylene chloride (500 mL) were added, and 1 mol/L HCl was added to adjust pH to 6. The mixture was then extracted twice. Methylene chloride layer was collected, combined, dried, and concentrated. The remaining mixture was purified by column chromatography to obtain compound 6 as a brownish yellow solid:

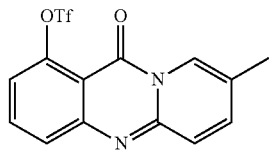

(68.9 g, 69%);

(6) Preparation of Compound 7

[1,1'-Bis(diphenylphosphino)ferrocene]palladium dichloride (7 g, 9.57 mmol) and triethylamine (58.38 g, 576.90 mmol) were added to a mixture of compound 6 (68.9 g, 192.30 mmol), methanol/N,N-dimethylformamide (volume ratio of 4:1, 700 mL). The mixture was reacted under CO atmosphere (recharged 3 times) at 85° C. and under 0.8 MPa for 10 hours. After TLC indicated that the reaction was complete, solvent was removed. Water (500 mL) and methylene chloride (800 mL) were added and extracted twice. The methylene chloride layer was collected, combined, dried, and concentrated. The remaining mixture was purified by column chromatography to obtain compound 7 as a brownish yellow solid:

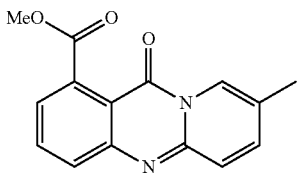 [SMILES: COC(=O)c1cccc2nc3ccc(C)cn3c(=O)c12]

(45.6 g, 88%);

(7) Preparation of Compound 8

Hydrazine hydrate (186.61 mg, 3.73 mg) was added to a mixture of compound 7 (500 mg, 1.86 mmol) and ethanol (5 mL). The mixture was reacted at room temperature for 8 hours. After TLC indicated that the reaction was complete, ethanol and hydrazine were removed. Water (20 mL) was added the mixture and the mixture was stirred. The mixture was filtered to obtain compound 8 as a yellow solid:

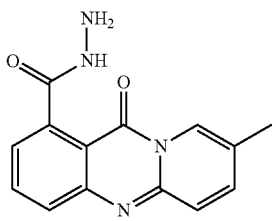 [SMILES: Cc1ccc2nc3cccc(C(=O)NN)c3c(=O)n2c1]

(408 mg, 82%);

(8) Preparation of Compound 9

Compound 8 from step (8) was added to 5 mL polyphosphoric acid, and the mixture was reacted at 150° C. for 8 hours. The mixture was poured into water (30 mL) to quench the polyphosphoric acid. Ammonia was added to the mixture to pH 8 while maintaining the temperature of the mixture not exceeding 30° C. Mixture was then filtered and dried to obtain compound 9 as a light yellow solid:

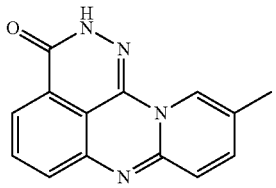 [SMILES: CC1=CN2C(=Nc3cccc4c(=O)[nH]nc2c34)C=C1]

(280 mg, 74%).

(9) Preparation of Compound 10

N-bromosuccinimide (19.79 g, 111.83 mmol) and azobisisobutyronitrile (1.53 g, 9.32 mmol) were added to a mixture of compound 7 (25 g, 93.19 mmol) and carbon tetrachloride (250 mL). The mixture was refluxed for 12 hours. After TLC indicates that the reaction was complete, water (500 mL) and methylene chloride (500 mL) were added and extracted twice. The methylene chloride layer was collected, combined, dried, and concentrated. The remaining mixture was purified by column chromatograph to obtain compound 10 as a golden compound:

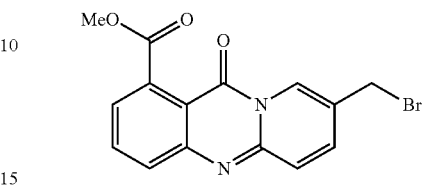

(20 g, 62%);

(10) Preparation of Compounds 14-26 (Compound 14 used as example)

2-Fluoroethylamine hydrochloride (157.69 mg, 5.76 mmol) and potassium carbonate (796.18 mg, 5.76 mmol) were added to a mixture of compound 10 (500 mg, 1.44 mmol) and acetonitrile (5 mL). The mixture was reacted at 55° C. for 8 hours. After TLC indicated that the reaction was complete, water (50 mL) and ethyl acetate (100 mL) were added and extracted twice. The ethyl acetate layer was collected, combined, dried, and concentrated to obtain compound 11 as a yellow oil:

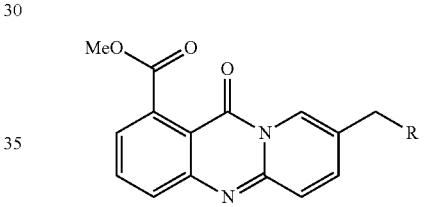

(380 mg, 80%);

Hydrazine hydrate (115.14 mg, 2.30 mmol) was added to a mixture of compound 11 from the above step and ethanol (5 mL). The mixture was reacted at room temperature for 8 hours. After TLC indicated that the reaction was complete, ethanol and hydrazine were removed. Water (50 mL) was added the mixture and the mixture was stirred. The mixture was filtered to obtain compound 12 as a yellow solid:

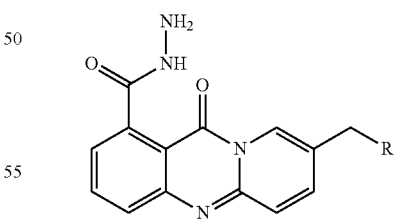

(287 mg, 76%).

Compound 12 from the above step was added to polyphosphoric acid (5 mL), and the mixture was reacted at 150° C. for 8 hours. The mixture was poured into water (30 mL) to quench the polyphosphoric acid. Ammonia was added to the mixture to pH 8 while maintaining the temperature of the mixture not exceeding 30° C. Mixture was then filtered and dried to obtain compound 14 as a light yellow solid (200 mg, 74%).

Replacing 2-fluoroethylamine hydrochloride with 2,2,2-trifluoroethylamine hydrochloride, diethylamine hydrochloride, pyrrolidine, imidazole, piperidine, morpholine, 4-tert-butoxycarbonylaminopiperidine, 4-dimethylaminopiperidine, 1-methyl-4-methylaminopiperidine, 1-phenyl-4-methylaminopiperidine, 1-benzyl-4-methylaminopiperidine or 7-fluoro-1,2,3,4-tetrahydroisoquinoline, other conditions remained the same, and compounds 15-26 were prepared. Note that, if the coupling compound is not a hydrochloride salt, the amount of potassium carbonate will be reduced by one equivalent.

EXAMPLE 3

An azaphenalene-3-one derivative has the following Formula (I):

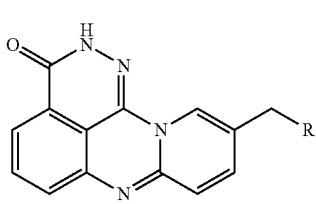

(I)

R is H, 2-fluoroethylamino, 2,2,2-trifluoroethylamino, diethylamino, pyrrolidinyl, imidazolyl, piperidinyl, morphinolinyl, 4-methylaminopiperidinyl, 4-dimethylaminopiperidinyl, (1-methylpiperidin-4-yl)methylamino, (1-phenylpiperidin-4-yl)methylamino, (1-benzylpiperidin-4-yl)methylamino, or 7-fluoro-3,4-dihydroisoquinoline-2(1H)-yl.

The azaphenalene-3-one derivative can be prepared by the following steps:

(1) Preparation of Compound 2

Pyridine (67.86 g, 857.84 mmol) was added to a mixture of 2-amino-6-methoxybenzoic acid (71.7 g, 428.92 mmol) and acetonitrile (720 mL). Triphosgene (43.27 g, 145.83 mmol) was added to the mixture while maintaining a reaction temperature not exceeding 30° C. The mixture was reacted at room temperature for 6 hours. After thin layer chromatograph (TLC) indicated that reaction was complete, 1 L water was added, and the mixture was filtered and dried to obtain a yellow-white solid compound 2:

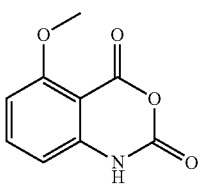

(70 g, 84%);

(2) Preparation of Compound 3

Sodium hydroxide (1.45 g, 36.24 mmol) was added in two batches to a mixture of compound 2 (70 g, 362.40 mmol) and methanol (700 mL). The mixture was reacted at 60° C. for 2 hours. After reaction was complete, methanol was removed. 500 ml Water and 1 L ethyl acetate were added and extracted twice. Ethyl acetate layer was collected, combined, dried, and concentrated. The remaining mixture was purified by column chromatograph to obtain compound 3 as a maroon solid:

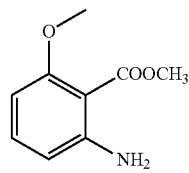

(52.1 g, 79%);

(3) Preparation of Compound 4

2-Bromo-5-methylpyridine (26.11 g, 151.77 mmol), cesium carbonate (66.08 g, 202.81 mmol), palladium acetate (0.90 g, 4.00 mmol), and 4,5-bisdiphenylphosphino-9,9-dimethyloxaxene (2.68 g, 4.63 mmol) were added to a mixture of compound 3 (25 g, 137.98 mmol) and dioxane (250 mL). The mixture was reacted under nitrogen atmosphere at 60° C. for 6 hours. After Thin Layer Chromatograph (TLC) indicated that the reaction was complete, 500 mL and 800 mL methylene chloride were added and extracted twice. Methylene chloride layer was collected, combined, dried and concentrated. The remaining mixture was purified by column chromatograph to obtain compound 4 as a light yellow solid:

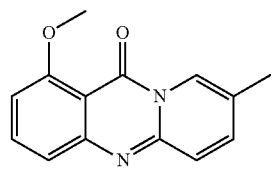 [SMILES: COc1cccc2nc3ccc(C)cn3c(=O)c12]

(24.6 g, 74%);

(4) Preparation of Compound 5

Compound 4 (24.6 g, 102.39 mmol) was added to methylene chloride (500 mL) to form a mixture. Boron tribromide (56.43 g, 225.25 mmol) was diluted with 110 mL methylene chloride. The diluted boron tribromide was added slowly to the compound 4 mixture while maintaining a reaction temperature not exceeding −20° C. Afterwards, the mixture was reacted at −10° C. for 3 hours. After TLC indicated that the reaction was complete, 150 mL water was added slowly to quench boron tribromide while maintaining a reaction temperature not exceeding −10° C. The reaction temperature was then raised to room temperature, and saturated sodium carbonate solution was added to the mixture to pH 7. 500 mL water and 800 mL methylene chloride were added and extracted once. Methylene chloride layer was collected, combined, dried and concentrated to obtain compound 5 as yellow solid:

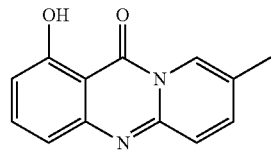 [SMILES: Cc1ccc2nc3cccc(O)c3c(=O)n2c1]

(20 g, 86%);

(5) Preparation of Compound 6

4-Dimethylaminopyridine (42.34 g. 346.55 mmol) was added to a mixture of compound 5 (49 g, 216.59 mmol) and methylene chloride (1 L). Trifluoromethanesulfonic anhydride (73.33 g, 259.91 mmol) was diluted with 150 mL methylene chloride. The diluted trifluoromethanesulfonic anhydride was added slowly to the mixture while maintaining a reaction temperature not exceeding −5° C. Afterwards, the reaction temperature was raised to room temperature, and the mixture was reacted for 0.5 hour. After TLC indicated that the reaction was complete, water (500 mL) and methylene chloride (500 mL) were added, and 1 mol/L HCl was added to adjust pH to 6. The mixture was then extracted twice. Methylene chloride layer was collected, combined, dried, and concentrated. The remaining mixture was purified by column chromatography to obtain compound 6 as a brownish yellow solid:

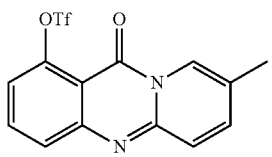 [SMILES: Cc1ccc2nc3cccc(OS(=O)(=O)C(F)(F)F)c3c(=O)n2c1]

(68.9 g, 69%);

(6) Preparation of Compound 7

[1,1'-Bis(diphenylphosphino)ferrocene]palladium dichloride (7 g, 9.57 mmol) and triethylamine (58.38 g, 576.90 mmol) were added to a mixture of compound 6 (68.9 g, 192.30 mmol), methanol/N,N-dimethylformamide (volume ratio of 4:1, 700 mL). The mixture was reacted under CO atmosphere (recharged 3 times) at 75° C. and under 0.8 MPa for 8 hours. After TLC indicated that the reaction was complete, solvent was removed. Water (500 mL) and methylene chloride (800 mL) were added and extracted twice. The methylene chloride layer was collected, combined, dried, and concentrated. The remaining mixture was purified by column chromatography to obtain compound 7 as a brownish yellow solid:

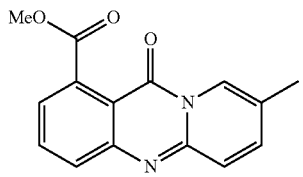

(45.6 g, 88%);

(7) Preparation of Compound 8

Hydrazine hydrate (186.61 mg, 3.73 mg) was added to a mixture of compound 7 (500 mg, 1.86 mmol) and ethanol (5 mL). The mixture was reacted at room temperature for 6 hours. After TLC indicated that the reaction was complete, ethanol and hydrazine were removed. Water (20 mL) was added the mixture and the mixture was stirred. The mixture was filtered to obtain compound 8 as a yellow solid:

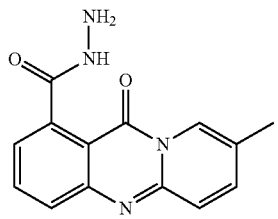

(408 mg, 82%);

(8) Preparation of Compound 9

Compound 8 from step (8) was added to 5 mL polyphosphoric acid, and the mixture was reacted at 140° C. for 6 hours. The mixture was poured into water (10 mL) to quench the polyphosphoric acid. Ammonia was added to the mixture to pH 8 while maintaining the temperature of the mixture not exceeding 30° C. Mixture was then filtered and dried to obtain compound 9 as a light yellow solid:

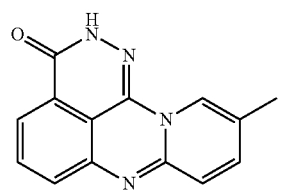 [SMILES: CC1=CN2C(=Nc3cccc4c(=O)[nH]nc2c34)C=C1]

(280 mg, 74%).

(9) Preparation of Compound 10

N-bromosuccinimide (19.79 g, 111.83 mmol) and azobisisobutyronitrile (1.53 g, 9.32 mmol) were added to a mixture of compound 7 (25 g, 93.19 mmol) and carbon tetrachloride (250 mL). The mixture was refluxed for 10 hours. After TLC indicates that the reaction was complete, water (500 mL) and methylene chloride (500 mL) were added and extracted twice. The methylene chloride layer was collected, combined, dried, and concentrated. The remaining mixture was purified by column chromatograph to obtain compound 10 as a golden compound:

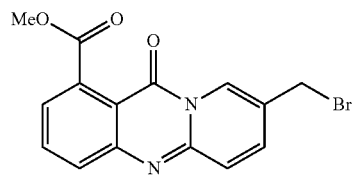 [SMILES: COC(=O)c1cccc2nc3ccc(CBr)cn3c(=O)c12]

(20 g, 62%);

(10) Preparation of Compounds 14-26 (Compound 14 used as example)

2-Fluoroethylamine hydrochloride (157.69 mg, 5.76 mmol) and potassium carbonate (796.18 mg, 5.76 mmol) were added to a mixture of compound 10 (500 mg, 1.44 mmol) and acetonitrile (5 mL). The mixture was reacted at 45° C. for 6 hours. After TLC indicated that the reaction was complete, water (50 mL) and ethyl acetate (100 mL) were added and extracted twice. The ethyl acetate layer was collected, combined, dried, and concentrated to obtain compound 11 as a yellow oil:

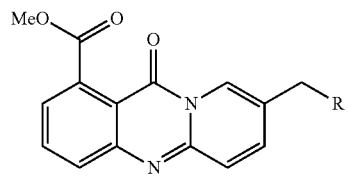

(380 mg, 80%);

Hydrazine hydrate (115.14 mg, 2.30 mmol) was added to a mixture of compound 11 from the above step and ethanol (5 mL). The mixture was reacted at room temperature for 6 hours. After TLC indicated that the reaction was complete, ethanol and hydrazine were removed. Water (50 mL) was added the mixture and the mixture was stirred. The mixture was filtered to obtain compound 12 as a yellow solid:

(287 mg, 76%).

Compound 12 from the above step was added to polyphosphoric acid (5 mL), and the mixture was reacted at 140° C. for 6 hours. The mixture was poured into water (30 mL) to quench the polyphosphoric acid. Ammonia was added to the mixture to pH 8 while maintaining the temperature of the mixture not exceeding 30° C. Mixture was then filtered and dried to obtain compound 14 as a light yellow solid (200 mg, 74%).

Replacing 2-fluoroethylamine hydrochloride with 2,2,2-trifluoroethylamine hydrochloride, diethylamine hydrochloride, pyrrolidine, imidazole, piperidine, morpholine, 4-tert-butoxycarbonylaminopiperidine, 4-dimethylaminopiperidine, 1-methyl-4-methylaminopiperidine, 1-phenyl-4-methylaminopiperidine, 1-benzyl-4-methylaminopiperidine or 7-fluoro-1,2,3,4-tetrahydroisoquinoline, other conditions remained the same, and compounds 15-26 were prepared. Note that, if the coupling compound is not a hydrochloride salt, the amount of potassium carbonate will be reduced by one equivalent.

Compound 9: $^1$H NMR (400 MHz, DMSO) δ=12.05 (s, 1H), 8.33 (s, 1H), 7.87 (t, J=7.9, 1H), 7.70 (d, J=6.8, 1H), 7.57 (dd, J=8.1, 0.9, 1H), 7.49 (dd, J=9.3, 2.0, 1H), 7.17 (d, J=9.2, 1H), 2.28 (d, J=1.0, 3H).

Compound 14: $^1$H NMR (400 MHz, D$_2$O) δ=9.25 (s, 1H), 8.27 (d, J=9.5, 1H), 8.00-7.83 (m, 2H), 7.61 (dd, J=15.2, 8.6, 2H), 4.91-4.76 (m, 2H), 4.45 (s, 2H), 3.50 (ddd, J=18.9, 11.9, 5.7, 2H).

Compound 15: $^1$H NMR (400 MHz, D$_2$O) δ=9.22 (s, 1H), 8.27 (d, J=8.8, 1H), 8.02-7.86 (m, 2H), 7.61 (dd, J=12.9, 8.6, 2H), 4.43 (s, 2H), 3.94 (q, J=8.9, 2H), 3.61-3.38 (m, 1H).

Compound 16: $^1$H NMR (400 MHz, D2O) δ=9.26 (t, J=7.8, 1H), 8.27 (dd, J=9.3, 1.9, 1H), 8.02-7.87 (m, 2H), 7.63 (t, J=8.3, 2H), 4.47 (s, 2H), 3.31-3.17 (m, 4H), 1.29 (t, J=7.3, 6H).

Compound 17: $^1$H NMR (400 MHz, D$_2$O) δ=9.31 (s, 1H), 8.33 (s, 1H), 7.98 (dd, J=21.0, 7.3, 2H), 7.67 (s, 2H), 4.56 (s, 2H), 3.61 (s, 2H), 3.24 (s, 2H), 2.09 (d, J=69.8, 4H).

Compound 18: $^1$H NMR (400 MHz, D$_2$O) δ=9.15 (s, 1H), 8.93 (s, 1H), 8.14 (d, J=9.4, 1H), 7.89 (t, J=8.0, 1H), 7.79 (d, J=7.8, 1H), 7.52 (dd, J=16.5, 11.5, 4H), 5.55 (d, J=16.6, 2H), 3.58-3.40 (m, 1H).

Compound 19: $^1$H NMR (400 MHz, D$_2$O) δ=9.25 (s, 1H), 8.27 (dd, J=9.3, 1.6, 1H), 7.94 (t, J=8.0, 1H), 7.86 (d, J=7.9, 1H), 7.60 (d, J=8.4, 2H), 4.41 (s, 2H), 3.55-3.46 (m, 2H), 3.00 (dd, J=12.5, 10.0, 2H), 1.89 (d, J=14.8, 2H), 1.79-1.58 (m, 3H), 1.40 (q, J=12.7, 1H).

Compound 20: $^1$H NMR (400 MHz, D$_2$O) δ=9.28 (s, 1H), 8.27 (d, J=9.5, 1H), 8.04-7.85 (m, 2H), 7.63 (dd, J=12.0, 8.6, 2H), 4.52 (s, 2H), 3.92 (s, 4H), 3.45 (dd, J=17.9, 12.4, 4H).

Compound 21: $^1$H NMR (400 MHz, D$_2$O) δ=9.31 (s, 1H), 8.30 (d, J=9.2, 1H), 8.06-7.86 (m, 2H), 7.65 (t, J=9.2, 2H), 4.51 (s, 2H), 3.71 (d, J=11.3, 2H), 3.60-3.49 (m, 1H), 3.45 (dd, J=11.8, 6.4, 1H), 3.23 (t, J=12.2, 2H), 2.67 (s, 3H), 2.38 (d, J=12.4, 2H), 1.91 (d, J=11.8, 2H).

Compound 22: $^1$H NMR (400 MHz, D$_2$O) δ=9.34 (s, 1H), 8.36 (s, 1H), 7.95 (t, J=17.6, 2H), 7.67 (s, 2H), 4.56 (s, 2H), 3.81 (s, 2H), 3.58 (dd, J=14.3, 7.1, 2H), 3.29 (s, 2H), 2.87 (s, 6H), 2.42 (s, 2H), 2.08 (s, 2H), 1.11 (t, J=7.0, 1H).

Compound 23: $^1$H NMR (400 MHz, D$_2$O) δ=9.33 (s, 1H), 8.29 (s, 1H), 8.00 (d, J=9.8, 2H), 7.68 (d, J=7.1, 2H), 4.57 (s, 2H), 3.84 (s, 1H), 3.68 (s, 2H), 3.56 (s, 1H), 3.15 (s, 2H), 2.82 (d, J=23.6, 5H), 2.41 (d, J=34.9, 2H), 2.15 (s, 2H).

Compound 24: $^1$H NMR (400 MHz, D$_2$O) δ=9.35 (s, 1H), 8.33 (d, J=9.2, 1H), 7.99 (dt, J=15.6, 7.8, 2H), 7.67 (t, J=7.8, 2H), 7.60-7.36 (m, 5H), 4.64 (s, 2H), 4.04 (t, J=11.9, 1H), 3.92 (d, J=12.9, 2H), 3.77 (t, J=12.0, 2H), 2.87 (s, 3H), 2.59 (d, J=13.7, 2H), 2.50-2.30 (m, 2H).

Compound 25: $^1$H NMR (400 MHz, D$_2$O) δ=9.32 (s, 1H), 8.29 (d, J=9.0, 1H), 8.09-7.90 (m, 2H), 7.74-7.57 (m, 2H), 7.44 (s, 5H), 4.56 (s, 2H), 4.30 (s, 1H), 3.85 (s, 1H), 3.69 (d, J=11.2, 2H), 3.60-3.50 (m, 1H), 3.45 (dd, J=11.8, 6.4, 1H), 3.17 (t, J=11.9, 2H), 2.78 (s, 2H), 2.45 (d, J=12.3, 2H), 2.11 (d, J=12.1, 2H).

Compound 26: $^1$H NMR (400 MHz, D$_2$O) δ=9.25 (s, 1H), 8.30 (d, J=9.5, 1H), 7.93 (t, J=8.1, 1H), 7.84 (d, J=8.0, 1H), 7.59 (t, J=7.9, 2H), 7.29-7.18 (m, 1H), 7.03 (dd, J=8.6, 6.6, 1H), 6.89 (d, J=9.5, 1H), 4.65 (s, 2H), 4.46 (s, 2H), 3.70 (s, 2H), 3.60-3.53 (m, 1H), 3.47 (dd, J=11.7, 6.5, 1H), 3.17 (s, 2H).

EXAMPLE 4

The azaphenalene-3-one derivatives 14-26 prepared according to Example 3 were sequentially named as compounds A1 to A13.

The activities of the azaphenalene-3-one derivatives were tested. The experimental methods are as follows:

Determination of PARP1 inhibitory activity

Experimental material: Universal PARP colorimetric assay kit (Trevigen): 10 U/µL PARP-HAS, 20X PARP Buffer, 10X PARP1 cocktail, histidine-containing 96-well plate, 200 mM 3-AB, 10X Strep-Diluen, Strep-HRP, TACS-Sapphire™, 10X Activated DNA; PBS solution; PBS+0.1% Triton X-100; distilled water; 0.02 M HCl; PARP1 small molecule inhibitors: Compounds 9; A1-A13.

Method for determining PARP1 inhibitory activity:

(1) adding 50 µL of 1X PARP Buffer to each well, incubating for 30 min at room temperature, and drying;

(2) adding PARP1 inhibitor at a series of concentrations, control 3-AB being 10 µM, adding 0.5 U of PARP-HAS to each well, and the total volume in the well being 25 µL, and incubating for 10 min at room temperature;

(3) adding 25 µL of 1X PARP1 cocktail to each well and incubating for 60 min at room temperature;

(4) washing twice with PBS+0.1% Triton X-100 and PBS, respectively, 200 µL each time, and drying to remove the residual solution; adding 50 µL of 1X Strep-HRP and incubating for 60 min at room temperature; after washing twice in the same procedure as above, adding TACS-Sapphire™, incubating at room temperature for 15 min in the dark, adding 50 µL of 0.2 M HCl, terminating the reaction, and measuring the OD value per well at 450 nM; calculating the IC$_{50}$ value (Logt-t method);

(5) calculating the inhibition rate as follows: PARP1 Enzyme Inhibition rate %=(Active Group OD value−Blank Control OD value)−(Inhibition group OD value−Blank Control OD)/(Active Group OD value−Blank Control OD value)×100%.

TABLE 1
Inhibitory Activity of Compound 9
| Compound | Inhibition[a] (%) | IC$_{50}$ (nM) |
|---|---|---|
| 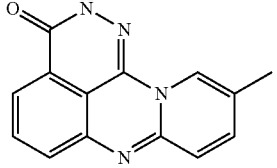 | 87.58% | 81.93 |
[a]Inhibition rate below 500 nM unless indicating otherwise.
TABLE 2
Inhibitory Activity of Compounds A1-A7
| Compound | R | Inhibition[a] (%) | IC$_{50}$ (nM) |
|---|---|---|---|
| 3-AB Standard Sample | 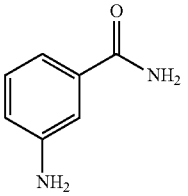 | 16.92% (inhibition rate, 10 μM) | 3100 |
| BSI-201 Positive Control Sample | 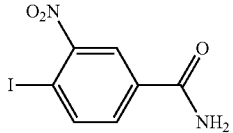 | 23.6% (inhibition rate, 1 μM) | ND |
| A1 |  | 85.97% | ND |
| A2 | 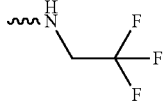 | 76.29% | 345.82 |
| A3 | 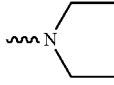 | 84.77% | 137.15 |
| A4 | 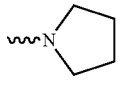 | 84.77% | 103.32 |
| A5 | 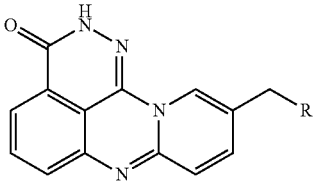 | 95.72% | 164.13 |
| A6 | 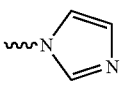 | 91.67% | 293.67 |

TABLE 2-continued

Inhibitory Activity of Compounds A1-A7

| Compound | R | Inhibition[a] (%) | IC$_{50}$ (nM) |
|---|---|---|---|
| A7 | 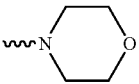 morpholine | 73.37% | 194.25 |

[a]Inhibition rate below 500 nM unless indicating otherwise
ND: Cannot be determined

TABLE 3

Inhibitory Activity of Compounds A1-A7

| Compound | R | Inhibition[a] (%) | IC$_{50}$ (nM) |
|---|---|---|---|
| A8 | 4-(methylamino)piperidinyl | 79.97% | ND |
| A9 | 4-(dimethylamino)piperidinyl | 82.15% | ND |
| A10 | 1-methyl-4-(methylamino)piperidine | 88.97% | 118.84 |
| A11 | 1-phenyl-4-(methylamino)piperidine | 92.42% | 160.50 |
| A12 | 1-benzyl-4-(methylamino)piperidine | 89.42% | ND |
| A13 | 7-fluoro-1,2,3,4-tetrahydroisoquinolinyl | 79.67% | ND |

[a]Inhibition rate below 500 nM unless indicating otherwise.
ND: Cannot be determined The present invention synthesized and purified a series of azaphenalene-3-one derivatives, confirmed the chemical structures by nuclear magnetic resonance spectroscopy (NMR), and measured PARP enzyme inhibition activity. The test results are shown in Tables 1-3. The IC$_{50}$ of compounds 9 and 14-26 were measure by the universal PARP colorimetric assay kit and were at the nM level, similar to the PARP inhibitors currently in clinical trials. These compounds showed good inhibitory activity against PARP enzymes, and also proved the rationality of the design.

What is claimed is:
1. A compound having Formula (I):

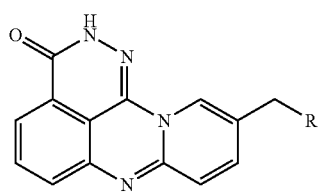

(I)

wherein R is H, 2-fluoroethylamino, 2,2,2-trifluoroethylamino, diethylamino, pyrrolidinyl, imidazolyl, piperidinyl, morphinolinyl, 4-methylaminopiperidinyl, 4-dimethylaminopiperidinyl, (1-methylpiperidin-4-yl)methylamino, (1-phenylpiperidin-4-yl)methylamino, (1-benzylpiperidin-4-yl)methylamino, or 7-fluoro-3,4-dihydroisoquinoline-2(1H)-yl.

2. A method of preparing the compound of claim 1, comprising the following steps:
(1) adding pyridine to a mixture of 2-amino-6-methoxybenzoic acid and acetonitrile, and adding triphosgene to the mixture while maintaining a reaction temperature not exceeding 30° C., a molar ratio of 2-amino-6-methoxybenzoic acid:pyridine:triphosgene being 1:2:0.3, a ratio of acetonitrile:reactants being 10 mL:1 g, reacting at room temperature for 5.5-8 hours,

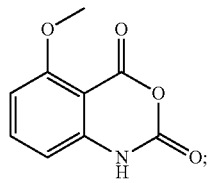

filtering the mixture and drying to obtain compound 2:
(2) adding sodium hydroxide in two batches to a mixture of compound 2 and methanol, a molar ratio of compound 2: sodium hydroxide being 1:0.1, a ratio of methanol:reactants being 10 mL:1 g, reacting at 50-70° C. for 1.5-3 hours, removing methanol after reaction is complete, extracting with ethyl acetate and water, colleting ethyl acetate, removing ethyl acetate, purifying with column chromatograph to obtain compound 3:

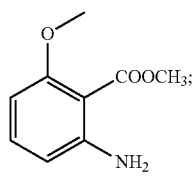

(3) adding 2-bromo-5-methylpyridine, cesium carbonate, palladium acetate, and 4,5-bisdiphenylphosphino-9,9-dimethyloxaxene to a mixture of compound 3 and dioxane, a molar ratio of compound 3:2-bromo-5-methylpyridine:cesium carbonate:palladium acetate:4,5-bisdiphenylphosphino-9,9-dimethyloxaxene being 1:1.1:1.5:0.1:0.3, a ratio of dioxane:reactants being 10 mL:1 g, reacting under nitrogen atmosphere at 50-75° C. for 5.5-8 hours, extracting with water and methylene chloride after reaction is complete, collecting methylene chloride, removing methylene chloride, purifying with column chromatograph to obtain compound 4:

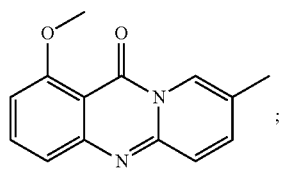 [SMILES: COc1cccc2nc3ccc(C)cn3c(=O)c12]

(4) adding compound 4 to methylene chloride to form a mixture, diluting boron tribromide with methylene chloride, adding diluted boron tribromide to the mixture while maintaining a reaction temperature not exceeding −20° C., a molar ratio of compound 4: boron tribromide being 1:2.2, a ratio of methylene chloride: reactants being 20 mL:1 g, methylene chloride being divided into 2 parts: first part being mixed with compound 4 and second part being diluted with boron tribromide, reacting at −5--15° C. for 2.5-4 hours, quenching reaction with water while maintaining a reaction temperature not exceeding −10° C., raising the reaction temperature to room temperature, adjusting pH to neutral with saturated sodium carbonate solution, extracting with water and methylene chloride, collecting methylene chloride, drying, removing methylene chloride to obtain compound 5:

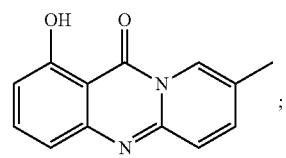 [SMILES: Cc1ccc2nc3cccc(O)c3c(=O)n2c1]

(5) adding 4-dimethylaminopyridine to a mixture of compound 5 and methylene chloride, diluting trifluoromethanesulfonic anhydride with methylene chloride, adding diluted trifluoromethanesulfonic anhydride to the mixture while maintaining a reaction temperature not exceeding −5° C., a molar ratio of compound 5:trifluoromethanesulfonic anhydride:4-dimethylaminopyridine being 1:1.2:1.6, a ratio of methylene chloride:reactants being 20 mL:1 g, methylene chloride being divided into two parts: first part being mixed with compound 5 and second part being diluted with trifluoromethanesulfonic anhydride, reacting at room temperature, adjusting pH to weakly acidic with HCl, extracting with water and methylene chloride, collecting methyl chloride, drying, removing methylene chloride, purifying with column chromatography to obtain compound 6:

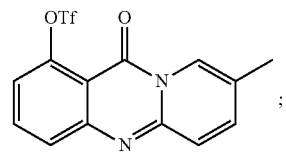 [SMILES: Cc1ccc2nc3cccc(OS(=O)(=O)C(F)(F)F)c3c(=O)n2c1]

(6) adding [1,1'-bis(diphenylphosphino)ferrocene]palladium dichloride and triethylamine to a mixture of compound 6, methanol, and N,N-dimethylformamide, [1,1'-bis(diphenylphosphino)ferrocene]palladium dichloride being a weight of 10% of the weight of compound 6, a molar ratio of compound 6: triethylamine being 1:3, a ratio of methanol and N,N-dimethylformamide:reactants being 10 mL:1 g, a volume ratio of methanol:N,N-dimethylformamide being 4:1, reacting with CO at 65-85° C. and under 0.8 MPa for 7.5-10 hours, removing methanol and N,N-dimethylformamide after reaction is complete, extracting with water and methylene chloride, collecting methylene chloride, drying, removing methylene chloride, purifying with column chromatograph to obtain compound 7:

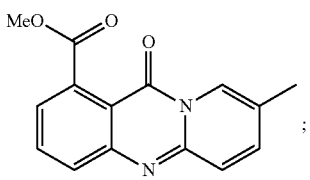 [SMILES: COC(=O)c1cccc2nc3ccc(C)cn3c(=O)c12]

(7) when R is H, adding hydrazine hydrate to a mixture of compound 7 and ethanol, a molar ratio of compound 7: hydrazine hydrate being 1:2, a ratio of ethanol:reactant being 10 mL:1 g, reacting at room temperature for 5.5-8 hours, removing ethanol and hydrazine hydrate after reaction is complete, adding water and stirring, filtering to obtain compound 8:

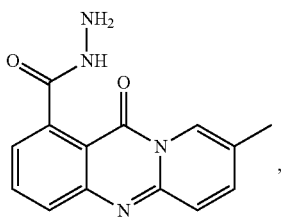

adding polyphosphoric acid to compound 8, a ratio of polyphosphoric acid:compound 8 being 10 mL:1 g, reacting at 130-150° C. for 5.5-8 hours, quenching with water, adjusting pH to weakly basic with ammonia to form participation, filtering to obtain compound 9:

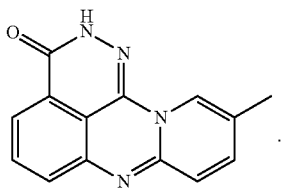 [SMILES: CC1=CN2C(=Nc3cccc4c(=O)[nH]nc2c34)C=C1]

3. A method of preparing the compound of claim 1, comprising the following steps:
(1) adding pyridine to a mixture of 2-amino-6-methoxybenzoic acid and acetonitrile, and adding triphosgene to the mixture while maintaining a reaction temperature not exceeding 30° C., a molar ratio of 2-amino-6-methoxybenzoic acid:pyridine:triphosgene being 1:2: 0.3, a ratio of acetonitrile:reactants being 10 mL:1 g, reacting at room temperature for 5.5-8 hours, filtering the mixture and drying to obtain compound 2:

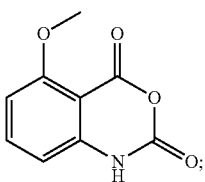

(2) adding sodium hydroxide in two batches to a mixture of compound 2 and methanol, a molar ratio of compound 2: sodium hydroxide being 1:0.1, a ratio of methanol:reactants being 10 mL:1 g, reacting at 50-70° C. for 1.5-3 hours, removing methanol after reaction is complete, extracting with ethyl acetate and water, colleting ethyl acetate, removing ethyl acetate, purifying with column chromatograph to obtain compound 3:

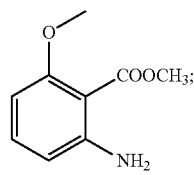

(3) adding 2-bromo-5-methylpyridine, cesium carbonate, palladium acetate, and 4,5-bisdiphenylphosphino-9,9-dimethyloxaxene to a mixture of compound 3 and dioxane, a molar ratio of compound 3: 2-bromo-5-methylpyridine:cesium carbonate:palladium acetate:4, 5-bisdiphenylphosphino-9,9-dimethyloxaxene being 1:1.1:1.5:0.1:0.3, a ratio of dioxane:reactants being 10 mL:1 g, reacting under nitrogen atmosphere at 50-75° C. for 5.5-8 hours, extracting with water and methylene chloride after reaction is complete, collecting methylene chloride, removing methylene chloride, purifying with column chromatograph to obtain compound 4:

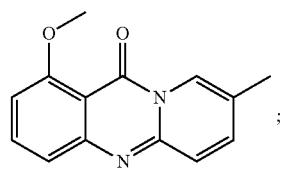 [SMILES: COc1cccc2nc3ccc(C)cn3c(=O)c12]

(4) adding compound 4 to methylene chloride to form a mixture, diluting boron tribromide with methylene chloride, adding diluted boron tribromide to the mixture while maintaining a reaction temperature not exceeding −20° C., a molar ratio of compound 4: boron tribromide being 1:2.2, a ratio of methylene chloride: reactants being 20 mL:1 g, methylene chloride being divided into 2 parts: first part being mixed with compound 4 and second part being diluted with boron tribromide, reacting at −5- −15° C. for 2.5-4 hours, quenching reaction with water while maintaining a reaction temperature not exceeding −10° C., raising the reaction temperature to room temperature, adjusting pH to neutral with saturated sodium carbonate solution, extracting with water and methylene chloride, collecting methylene chloride, drying, removing methylene chloride to obtain compound 5:

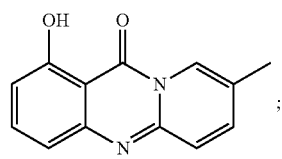 [SMILES: Cc1ccc2nc3cccc(O)c3c(=O)n2c1]

(5) adding 4-dimethylaminopyridine to a mixture of compound 5 and methylene chloride, diluting trifluoromethanesulfonic anhydride with methylene chloride, adding diluted trifluoromethanesulfonic anhydride to the mixture while maintaining a reaction temperature not exceeding −5° C., a molar ratio of compound 5: trifluoromethanesulfonic anhydride:4-dimethylaminopyridine being 1:1.2:1.6, a ratio of methylene chloride:reactants being 20 mL:1 g, methylene chloride being divided into two parts: first part being mixed with compound 5 and second part being diluted with trifluoromethanesulfonic anhydride, reacting at room temperature, adjusting pH to weakly acidic with HCl, extracting with water and methylene chloride, collecting methyl chloride, drying, removing methylene chloride, purifying with column chromatography to obtain compound 6:

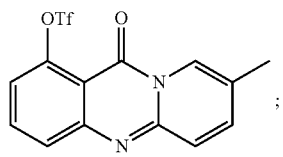 [SMILES: Cc1ccc2nc3cccc(OS(=O)(=O)C(F)(F)F)c3c(=O)n2c1]

(6) adding [1,1'-bis(diphenylphosphino)ferrocene]palladium dichloride and triethylamine to a mixture of compound 6, methanol, and N,N-dimethylformamide, [1,1'-bis(diphenylphosphino)ferrocene]palladium dichloride being a weight of 10% of the weight of compound 6, a molar ratio of compound 6: triethylamine being 1:3, a ratio of methanol and N,N-dimethylformamide:reactants being 10 mL:1 g, a volume ratio of methanol:N,N-dimethylformamide being 4:1, reacting with CO at 65-85° C. and under 0.8 MPa for 7.5-10 hours, removing methanol and N,N-dimethylformamide after reaction is complete, extracting with water and methylene chloride, collecting methylene chloride, drying, removing methylene chloride, purifying with column chromatograph to obtain compound 7:

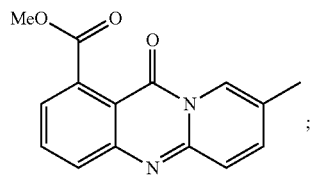 [SMILES: COC(=O)c1cccc2nc3ccc(C)cn3c(=O)c12]

(7) when R is not H, adding N-bromosuccinimide and azobisisobutyronitrile to a mixture of compound 7 and carbon tetrachloride, refluxing the mixture for 9.5-12 hours, the molar ratio of compound 7: N-bromosuccinimide:azobisisobutyronitrile being 1:1.2:0.1, a ratio of carbon tetrachloride:reactants being 20 mL:1 g, extracting with water and methylene chloride, collecting methylene chloride, drying, removing methylene chloride, purifying with column chromatograph to obtain compound 10:

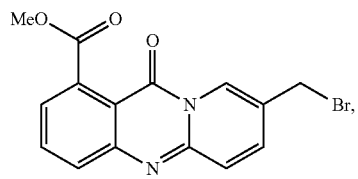

adding a coupling compound and potassium carbonate to a mixture of compound 10 and acetonitrile, a molar ratio of compound 10: the coupling compound:potassium carbonate being 1:1.1:4, a ratio of acetonitrile:reactants being 10 mL:1 g, reacting at 35-55° C. for 5.5-8 hours, extracting with water and ethyl acetate, collecting ethyl acetate, drying, and removing ethyl acetate to obtain compound 11:

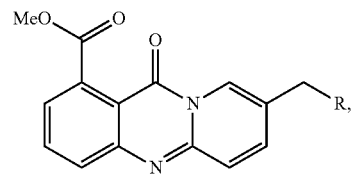

wherein the coupling compound is 2-fluoroethylamine hydrochloride, 2,2,2-trifluoroethylamine hydrochloride, diethylamine hydrochloride, pyrrolidine, imidazole, piperidine, morpholine, 4-tert-butoxycarbonylaminopiperidine, 4-dimethylaminopiperidine, 1-methyl-4-methylaminopiperidine, 1-phenyl-4-methylaminopiperidine, 1-benzyl-4-methylaminopiperidine or 7-fluoro-1,2,3,4-tetrahydroisoquinoline, adding hydrazine hydrate to a mixture of compound 11 and ethanol, a molar ratio of hydrazine hydrate:compound 11 being 2:1, a ratio of ethanol:reactant being 10 mL:1 g, reacting at room temperature for 5.5-8 hours, removing ethanol and hydrazine hydrate after reaction is complete, adding water and stirring, filtering to obtain compound 12:

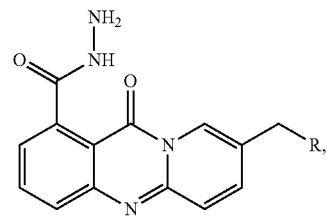

adding polyphosphoric acid to compound 12, a ratio of polyphosphoric acid:compound 8 being 10 mL:1 g, reacting at 130-150° C. for 5.5-8 hours, quenching with water, adjusting pH to weakly basic with ammonia to form participation, filtering to obtain compound 13:

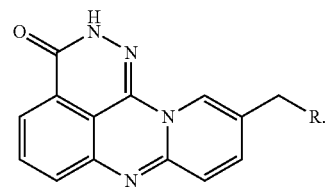

4. The method according to claim 2, wherein the completion of the reaction is monitored by thin layer chromatography.

5. The method according to claim 3, wherein the completion of the reaction is monitored by thin layer chromatography.